United States Patent

Van

[11] Patent Number: 5,855,478
[45] Date of Patent: Jan. 5, 1999

[54] METHOD FOR PREVENTING BACK FLOW IN A DENTAL SALIVA EJECTOR

[76] Inventor: Bryan B. Van, 3624 E. Paradise Dr., Phoenix, Ariz. 85028

[21] Appl. No.: 960,802

[22] Filed: Oct. 30, 1997

[51] Int. Cl.$^6$ .................................................. A61C 17/06
[52] U.S. Cl. ............................................ 433/95; 604/247
[58] Field of Search ............................. 433/95; 604/247, 604/249

[56] References Cited

U.S. PATENT DOCUMENTS

| | | | |
|---|---|---|---|
| 3,417,750 | 12/1968 | Carson | 128/278 |
| 3,463,159 | 8/1969 | Heimlich | 128/350 |
| 4,735,607 | 4/1988 | Keith, Jr. | 604/247 |
| 4,758,224 | 7/1988 | Siposs | 604/247 |
| 4,904,236 | 2/1990 | Redmond et al. | 604/247 |
| 4,966,551 | 10/1990 | Betush | 433/95 |
| 5,114,342 | 5/1992 | Young et al. | 433/95 |
| 5,425,637 | 6/1995 | Whitehouse et al. | 433/95 |
| 5,464,397 | 11/1995 | Powers, Jr. | 604/246 |
| 5,725,374 | 3/1998 | Young | 433/95 |

*Primary Examiner*—John J. Wilson
*Attorney, Agent, or Firm*—Meschkow & Gresham, P.L.C.; Jordan M. Meschkow; Lowell W. Gresham

[57] ABSTRACT

A unidirectional valve (46) is used for preventing a back flow (52) of fluid matter (72) in a dental saliva ejector (20). The unidirectional valve (46) includes a valve body (74) and a valve diaphragm (76). The valve diaphragm (76) is coupled to a base (78) of the valve body (74). The base (78) has apertures (90) for separating a particulate component (104) from a liquid component (102) of fluid matter (72). The valve diaphragm (76) has a flexible flap (96) for allowing a forward flow (48) of liquid component (102) into a low volume suction tube (28) of saliva ejector (20). The flexible flap (96) is further configured to prevent the back flow (52) liquid component (102) into an ejector tip (26) and into the mouth (22) of a dental patient (24).

2 Claims, 3 Drawing Sheets

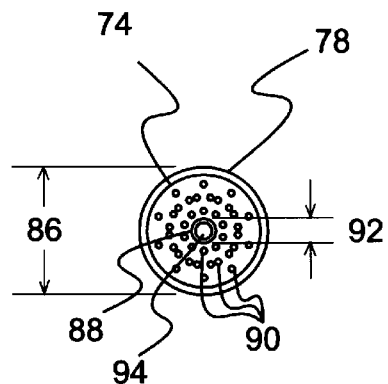
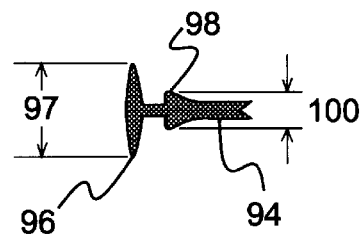
FIG. 4　　　　　　　　　　FIG. 5
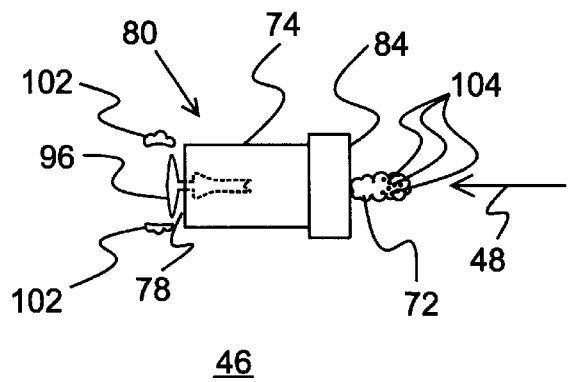
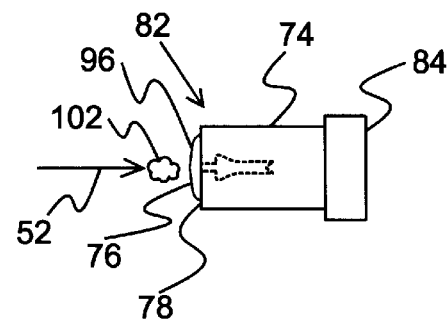
FIG. 6　　　　　　　　　　FIG. 7

METHOD FOR PREVENTING BACK FLOW IN A DENTAL SALIVA EJECTOR

TECHNICAL FIELD OF THE INVENTION

The present invention relates generally to the field of dental instruments, and specifically to the area of dental saliva ejectors. In particular, the present invention relates to a device for preventing back flow of fluid matter and oral contaminants in a dental saliva ejector.

BACKGROUND OF THE INVENTION

A saliva ejector is an apparatus which includes a suction line and a saliva ejector tip. The saliva ejector tip is inserted into the patient's mouth and suction is applied via the suction line to evacuate saliva and other debris from the patient's mouth. Per convention, the saliva ejector tip is a single use device that is replaced between each patient, while the suction line may be replaced or cleaned after it has been used with several patients. Unfortunately, fluids from the previous dental patient or patients may remain in the suction line when the saliva ejector is used on subsequent patients.

A common practice is to have patients close their lips around the low-volume saliva ejector tip and "spit" to help evacuate the mouth. Closing the lips around the ejector tip can cause a decrease in the vacuum line pressure. This may allow the previously evacuated fluid remaining in the suction line to flow backwards, or back flow, into the patient's mouth. This fluid can carry oral contaminants such as blood, viruses, bacteria, and fungi. It has been found that oral bacteria can survive inside of the suction line, and that diseases including influenza, strep, and hepatitis B could be passed to subsequent patients if the suction line back flows into the patient's mouth.

In order to decrease the possibility of the back flow of fluids into a dental patient's mouth, dentists and hygienists may instruct their patients not to close their lips around the saliva ejector tips so as to prevent a decrease in the vacuum line pressure. However, a problem exists with this approach in that the saliva ejector tip may still get wedged in a position in the patient's mouth, for instance in the cheek folds, to cause a decrease in the vacuum line pressure resulting in back flow.

Another approach for decreasing the chance of oral contaminants being passed from patient to patient is to clean or change the suction line after every patient. However, this approach is time consuming and cost prohibitive. Furthermore, if the suction line is rinsed with a germ killing rinse, any remaining rinse residue in the suction line may back flow into a subsequent patient. This circumstance would be unpleasant for the dental patient or possibly dangerous depending on the caustic nature of the rinse.

In one prior art saliva ejector, the saliva ejector tip includes at least one unregulated vacuum release aperture. This aperture is simply a hole made in a tubular sidewall of the ejector tip and is spaced from the mouthpiece of the saliva ejector tip such that when the mouthpiece is inserted into a patient's mouth, the patient's mouth will not block the aperture. If the patient's lips close around the mouthpiece, a vacuum will not develop because air from the room will be drawn through the aperture. A problem with this device is that the fluid matter may leak out of the aperture when the patient's mouth is being evacuated which causes oral contaminants to be released into the room.

Another prior art device is a saliva ejector tip with an integral valve. The valve system is made up of an internal plunger in the end of the ejector tip and is inserted into the patient's mouth. This plunger is pushed into a valve seat to close off the tip thereby eliminating the sucking noise produce by the saliva ejector. The dental personnel or the patient can then close off the tip with a hand when the ejector tip is removed from the mouth or the patient can close the valve using his or her teeth. Unfortunately, this device exacerbates the back flow problem because this configuration intentionally causes a decrease in the vacuum line pressure which results in back flow.

Yet another prior art device is a valve which includes a chamber and a tubular member positioned in the chamber. The tubular member has one or more reversely lipped fins for providing a tortuous path to limit back flow of oral contaminants. However, a problem with this device is that it does not prevent the back flow or oral contaminants, it merely limits the flow. Furthermore, due to the complex construction of this valve, it is difficult to clean and costly for single use applications.

SUMMARY OF THE INVENTION

Accordingly, an advantage of the present invention is that a valve and method for preventing back flow of fluid matter in a dental saliva ejector are provided.

Another advantage of the present invention is that a valve and method are provided that are readily incorporated into existing saliva ejectors.

Yet another advantage of the present invention is that a valve is provided that may be readily fabricated of inexpensive discardable material.

The above and other advantages of the present invention are carried out in one form by a unidirectional valve for preventing a back flow of fluid matter in a dental saliva ejector. The saliva ejector has an ejector tip and a low volume suction tube. The valve includes a valve body located between the ejector tip and the low volume suction tube. The valve also includes a valve diaphragm coupled to a base of the valve body. The valve diaphragm is configured to allow a forward flow of the fluid matter from the ejector tip to the low volume suction tube and to prevent the back flow of the fluid matter from the suction tube to the ejector tip.

The above and other advantages of the present invention are carried out in another form by a unidirectional ejector tip for preventing a back flow of fluid matter in a dental saliva ejector that has a low volume suction tube. The ejector tip includes an ejector tube configured to receive the fluid matter from the mouth of a patient. An interfacing socket has a first end configured to retain the ejector tube and a second end configured to retain the low volume suction tube. The interfacing socket has an inner shoulder and an axially aligned socket channel through the inner shoulder. A unidirectional valve is coupled to the inner shoulder of the interfacing socket. The unidirectional valve is configured to allow a forward flow of the fluid matter from the ejector tube through the socket channel into the low volume suction tube. The valve is further configured to prevent the back flow of the fluid matter from the suction tube into the ejector tube.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

FIG. 4 shows the base of a valve body that forms part of the unidirectional valve;

FIG. 5 shows a side view of a valve diaphragm that forms part of the unidirectional valve;

FIG. 6 shows a side view of a unidirectional valve in an open position; and

FIG. 7 shows a side view of the unidirectional valve in a closed position; and

DETAILED DESCRIPTION OF THE PREFERRED EMBODIMENTS

Figure 1:
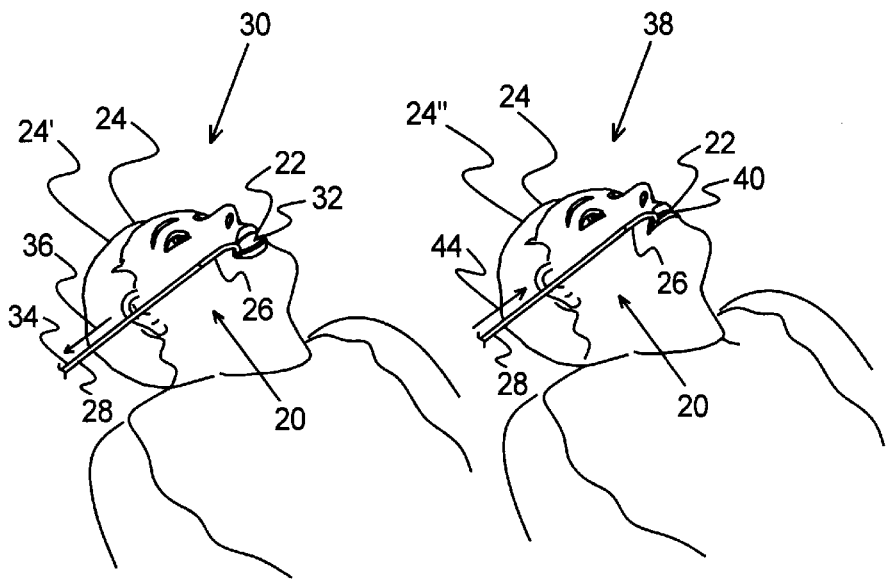
FIG. 1 shows dual views of a saliva ejector in the mouth of a patient.

FIG. 1 shows dual views of a saliva ejector 20 in the mouth 22 of a dental patient 24. Saliva ejector 20 includes an ejector tip 26 configured to be placed in mouth 22. Saliva ejector 20 also includes a suction tube 28 whose lower end (not shown) is connected to a low volume vacuum source (not shown). During a dental procedure, ejector tip 26 is inserted into mouth 22 to remove by suction any saliva and small particles, such as excess filling material, ground-away old fillings, decay, and so forth.

Patient 24 is depicted in two scenarios. In a first scenario 30, patient 24 is a patient 24' with mouth 22 in an open position 32. When the low volume vacuum source (not shown) is activated, a first differential pressure 34 results in suction tube 28. First differential pressure 34 is less than the ambient pressure at ejector tip 26 in mouth 22, therefore a forward flow occurs in the direction shown by an arrow 36 to evacuate mouth 22 of fluid matter (not shown).

Patient 24 is depicted in a second scenario 38 to illustrate back flow in saliva ejector 20. In second scenario 38, patient 24 is a patient 24" with mouth 22 in a closed position 40. When mouth 22 is closed and the aspirator holes (not shown) in ejector tip 26 are blocked, a second differential pressure 42 results in ejector tip 26. Second differential pressure 42 is less than the pressure in suction tube 28, therefore without the incorporation of the present invention, a back flow of fluid matter may occur in the direction shown by an arrow 44 to eject fluid matter into mouth 22.

Figure 2:
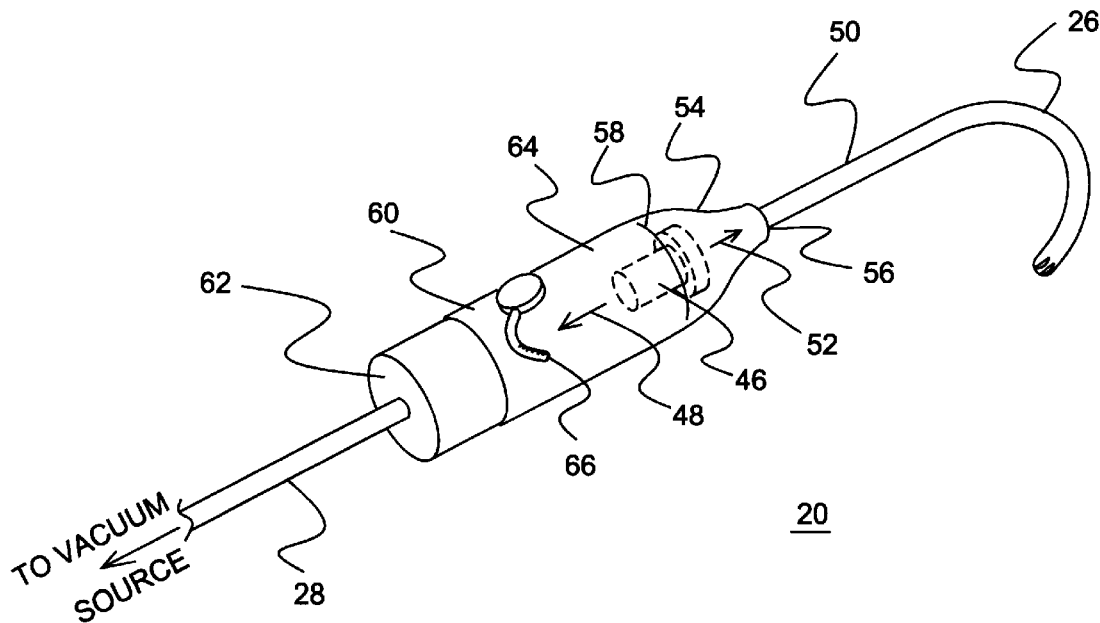
FIG. 2 shows a perspective view of a saliva ejector with a unidirectional valve located therein.

FIG. 2 shows a perspective view of saliva ejector 20 with a unidirectional valve 46 incorporated therein. Valve 46 allows a forward flow 48 of fluid matter (discussed below) from an ejector tube portion 50 of ejector tip 26 into low volume suction tube 28 and prevents a back flow 52 of fluid matter (not shown) from suction tube 28 into tube portion 50 of ejector tip 26.

In the preferred embodiment, saliva ejector 20 includes an interfacing socket 54. Interfacing socket 54 has a first end 56 and a second end 58. First end 56 is configured to retain ejector tip 26 by press fitting ejector tip 26 into first end 56.

Saliva ejector 20 also includes a suction controller 60. Suction controller 60 has a third end 62 and a fourth end 64. Third end 62 is configured to retain suction tube 28 by press fitting suction tube 28 onto a stem (not shown). Fourth end 64 of suction controller 60 mates with second end 58 of interfacing socket 54 either by press fitting together or by threaded engagement where both fourth and second ends 64 and 58 have coupling threads internally and externally, respectively.

Suction controller 60 is configured to allow the vacuum source (not shown), which produces first differential pressure 34 (FIG. 1), to draw fluid matter from ejector tip 26. The suction is controlled by adjusting a lever 66 on suction controller 60. Unidirectional valve 46 is located within interfacing socket 54 and suction controller 60 at the location where second end 58 and fourth end 64 mate.

Figure 3:
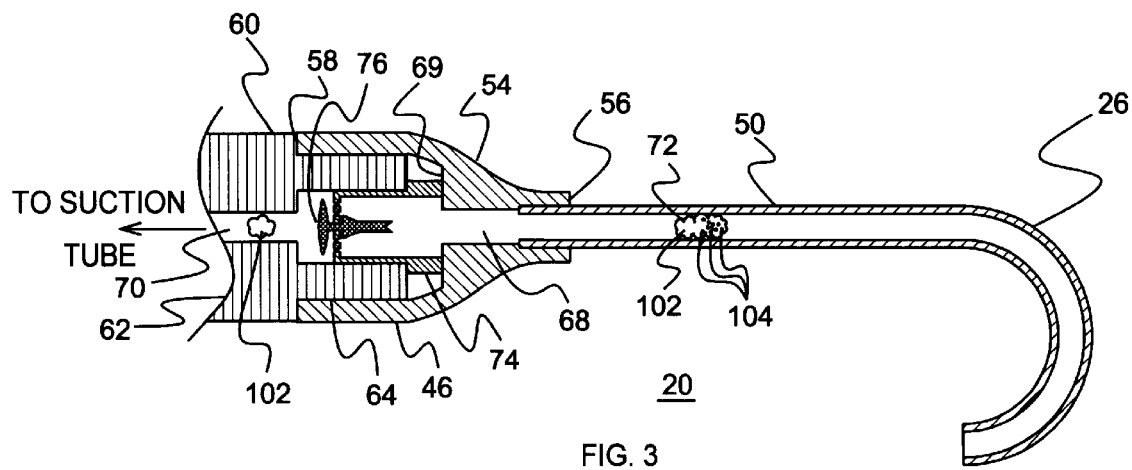
FIG. 3 shows a sectional view of the saliva ejector.

FIG. 3 shows a sectional view of saliva ejector 20. Interfacing socket 54 has an axially aligned socket channel 68 passing from first end 56 through an inner shoulder 69 of interfacing socket 54 and through second end 58. Likewise, suction controller 60 has an axially aligned controller channel 70 passing from fourth end 64 through third end 62. Unidirectional valve 46 is located in socket channel 68 and controller channel 70 between ejector tip 26 and low volume suction tube 28 (FIG. 2) to form a passage through which fluid matter 72 passes. Unidirectional valve 46 includes a valve body 74 and a valve diaphragm 76.

Referring collectively to FIGS. 4–7, FIG. 4 shows a base 78 of valve body 74 that forms part of unidirectional valve 46. FIG. 5 shows a side view of valve diaphragm 76 that forms part of unidirectional valve 46. FIG. 6 shows a side view of unidirectional valve 46 in an open position 80. Finally, FIG. 7 shows a side view of unidirectional valve 46 in a closed position 82.

Valve body 74 has a retaining end 84 which is configured to be coupled to inner shoulder 69 (FIG. 3) of interfacing socket 54 (FIG. 3). Base 78 of valve body 74 exhibits a base diameter 86. Valve body 74 is configured to fit in socket and controller channels 68 and 70, respectively (FIG. 3). Base 78 has a central opening 88 and a plurality of apertures 90. Central opening 88 exhibits an inner diameter 92.

Valve diaphragm 76 includes a shaft 94 and a flexible flap 96. Shaft 94 has a retaining collar 98 which exhibits an outer diameter 100. Outer diameter 100 is greater than inner diameter 92 of central opening 88 in base 78. This configuration allows shaft 94 to be passed through central opening 88 such that retaining collar 98 is forced through central opening 88, to retain shaft 94 in central opening 88.

Flexible flap 96 exhibits a flap diameter 97 that is no greater than base diameter 86. Additionally, unidirectional valve 46 is located in socket and controller channels 68 and 70, respectively, such that flexible flap 96 of valve diaphragm 76 is free to flex to open position 80 and closed position 82.

Flexible flap 96 is configured to flex to open position 80 relative to base 78 in response to first differential pressure 34 (FIG. 1) present in low volume suction tube 28 (FIG. 1) to allow passage of fluid matter 72 through ejector valve 46. Flexible flap 96 is further configured to flex to closed position 82 in response to second differential pressure 42 (FIG. 1) present in ejector tip 26 (FIG. 1).

Fluid matter 72 from mouth 22 (FIG. 1) includes a liquid component 102, such as saliva, water, and blood, and a particulate component 104, such as excess filling material, ground-away old fillings, and decay. When flexible flap 96 is in open position 80, apertures 90 (FIG. 4) located in base 78 allow forward flow 48 of liquid component 102 into suction tube 28 and retain particulate component 104 in valve body 74. When flexible flap 98 is in closed position 82, back flow 52 of liquid component 102 is prevented, thus preventing liquid component 102 and particulate component 104 from flowing back through ejector tip 26 and into mouth 22 (FIG. 1).

Unidirectional valve 46 is formed from plastic materials. For example, valve body 74 is formed from a stiff, strong resin type plastic and valve diaphragm is formed from a flexible rubber material such as vinyl or silicon. These materials are inexpensive and easily manufactured, so that valve 46 is readily discardable after a single use. Furthermore, unidirectional valve 46 is sized to fit into conventional saliva ejectors in place of the filter basket typically found between the ejector tip and the low volume suction tube. Therefore, unidirectional valve 46 is readily incorporated into existing saliva ejector systems and can be replaced between each dental patient at the same time that ejector tip 26 (FIG. 2) is being replaced so that the back flow of oral contaminants between dental patients is easily and inexpensively prevented.

Figure 8:
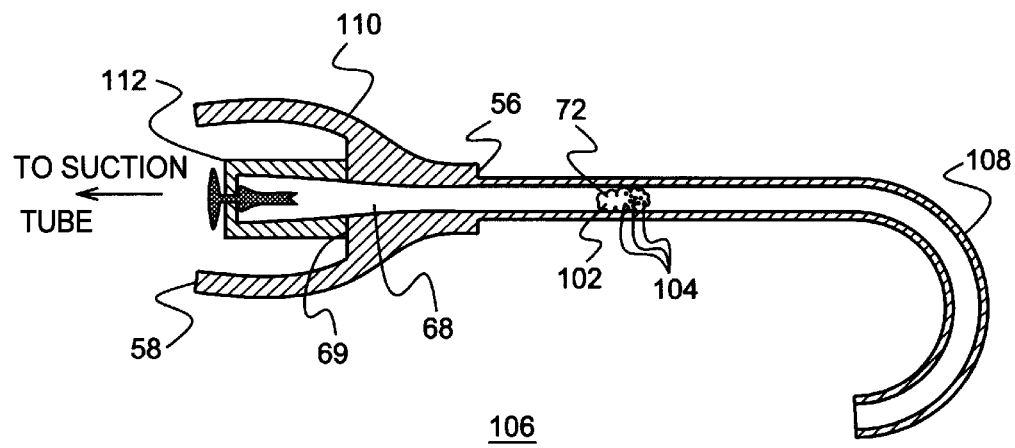
FIG. 8 shows a unidirectional ejector tip in an alternate embodiment of the present invention.

FIG. 8 shows a unidirectional ejector tip 106 in an alternate embodiment of the present invention. Unidirectional ejector tip 106 prevents the back flow of fluid matter 72 in a dental saliva ejector 20 (FIG. 1). Unidirectional ejector tip 106 includes an ejector tube 108, an interfacing socket 110, and a unidirectional valve 112 formed as a single unit.

Like saliva ejector 20 (FIG. 3), ejector tube 108 is configured to receive fluid matter 72 from mouth 22 (FIG. 1) of patient 24 (FIG. 1). Interfacing socket 110 has a first end 56 configured to retain ejector tube 108, a second end 58 configured to retain low volume suction tube 28 (FIG. 1), and an inner shoulder 69. Interfacing socket 110 has an axially aligned socket channel 68 through inner shoulder 69. Interfacing socket 110 exhibits the features of interfacing socket 54 (FIG. 3) and will not be described in detail herein.

Unidirectional valve 112 is coupled to inner shoulder 69 of interfacing socket 110. Valve 112 is configured to allow a forward flow of fluid matter 72 from ejector tube 108 through socket channel 68 into low volume suction tube 28. Valve 112 also prevents back flow of fluid matter 72 from suction tube 28 into ejector tube 108. Unidirectional valve 112 exhibits the features of unidirectional valve 46 and will not be described in detail herein.

Unidirectional ejector tip 106 is configured to connect to suction controller 60, which is a semi-permanent component generally made of autoclaveable stainless steel, of saliva ejector 20. Unidirectional ejector tip 106 is formed from plastic materials such that the unidirectional ejector tip is readily replaceable after a single use.

A method for preventing the back flow of fluid matter containing liquid and particulate into the mouths of each of a plurality of dental patients undergoing a dental procedure includes the following steps. The method includes allowing the flow of fluid matter 72 in a first direction, or forward flow 48, through unidirectional valve 46 of saliva ejector 20. Particulate component 104 is separated from liquid component 102 in base 78 of valve body 74. Liquid component 102 is then ejected through low volume suction tube 28. Flow of liquid component 102 is prevented in a second direction, or back flow 52, by the closure of flexible flap 96 in response to second differential pressure 42 (FIG. 1). Finally, unidirectional valve 46 or unidirectional ejector tip 106 with the integral unidirectional valve 112 is replaced between each of the patients in order to remove particulate component 104 that was separated from fluid component 102 in base 78.

In summary, the present invention provides a unidirectional valve and a method for preventing the back flow of fluid matter containing oral contaminants in a dental saliva ejector. Furthermore, the unidirectional valve is readily incorporated into conventional saliva ejectors. In addition, the unidirectional valve is readily fabricated of inexpensive material so that the unidirectional valve is a disposable, single use component of the saliva ejector.

Although the preferred embodiments of the invention have been illustrated and described in detail, it will be readily apparent to those skilled in the art that various modifications may be made therein without departing from the spirit of the invention or from the scope of the appended claims. For example, the unidirectional valve may couple directly to the low volume suction valve instead of the suction controller as described.

What is claimed is:

1. A method for preventing a back flow of fluid matter from a dental saliva ejector into the mouths of each of a plurality of dental patients undergoing a dental procedure, said fluid matter having a liquid component and a particulate component, said dental saliva ejector having a unidirectional valve, and said method comprising the steps of:

allowing flow of said fluid matter in a first direction;

separating said particulate component from said liquid component;

ejecting said liquid component;

preventing flow of said liquid component in a second direction, said second direction being a direction for said back flow; and replacing said unidirectional valve between each of said patients to remove said particulate component separated in said separating step.

2. A method as claimed in claim 1 wherein said unidirectional valve includes a flexible flap, said flap flexing to an open position in response to said allowing step and said flap flexing to a closed position in response to said preventing step.

\* \* \* \* \*